United States Patent [19]

Varadi et al.

[11] Patent Number: 5,643,739
[45] Date of Patent: Jul. 1, 1997

[54] ASSAY FOR DETERMINING SENSITIVITY TO ACTIVATED PROTEIN C

[75] Inventors: Katalin Varadi; Hans Peter Schwarz; Hartmut Lang; Berta Moritz, all of Vienna, Austria

[73] Assignee: Immuno AG, Vienna, Austria

[21] Appl. No.: 432,018

[22] Filed: May 1, 1995

Related U.S. Application Data

[63] Continuation of Ser. No. 160,877, Dec. 3, 1993, abandoned.

[51] Int. Cl.$^6$ .............................. C12Q 1/56; G01N 33/86; C07K 1/00
[52] U.S. Cl. .............................. 435/13; 435/810; 436/69; 436/808; 514/834; 530/381; 530/383; 530/384; 424/529
[58] Field of Search .................. 435/13, 810; 436/69, 436/808; 514/834; 530/381, 383, 384; 424/529

[56] References Cited

U.S. PATENT DOCUMENTS 4,672,030  6/1987  Witt ............................................. 435/13

FOREIGN PATENT DOCUMENTS

| | | |
|---|---|---|
| 0 434 377 | 6/1991 | European Pat. Off. . |
| 0 496 723 | 7/1992 | European Pat. Off. . |
| 91/01382 | 2/1991 | WIPO . |
| WO93/10261 | 5/1993 | WIPO . |
| 9310261 | 5/1993 | WIPO . |

OTHER PUBLICATIONS

Wagenvoord et al., *Haemostasis*, vol. 19, pp. 196–204, 1989.

Esmon, "Protein S and Protein C: Biochemistry, Physiology, and Clinical Manifestation of Deficiencies," *TCM*, vol.2, No. 6 (1992).

Dahlback et al., "Familial Thrombophilia Due to a Previously Unrecognized Mechanism Characterized by Poor Anticoagulant Response to Activated Protein C: Prediction of a Cofactor to Activated Protein C", *Proc. Natl. Acad. Sci.*, vol. 90, pp. 1004–1008 (1993).

Bokarewa et al., "Heterogeneity of the APC–Resistance Phenomenon", *Thrombosis Research*, vol. 75, No. 4, pp. 395–400, (1994).

Shen et al., "Factor V and Protein S As Synergistic Cofactors To Activated Protein C In Degradation of Factor VIIIa", *The Journal of Biological Chemistry*, vol. 269, No. 29, pp. 18735–18738, (1994).

Varadi et al., "A Chromogenic Assay For Activated Protein C Resistance", *British Journal of Haematology*, vol. 90:884–891, (1995).

*Primary Examiner*—Cecilia J. Tsang
*Assistant Examiner*—Abdel A. Mohamed
*Attorney, Agent, or Firm*—Foley & Lardner

[57] ABSTRACT

An improved assay for determining sensitivity to activated protein C in test samples has been developed to ensure rapid and accurate evaluations. This assay is based on measuring the conversion, by activated factor VIII within a test sample, of added factor X to an activated form. The activated protein C sensitivity of the test sample is determined by the relative inhibition of factor X conversion as compared to a control. A test sample that has decreased sensitivity to activated protein C will show relatively low inhibition, and vice versa.

18 Claims, No Drawings

ASSAY FOR DETERMINING SENSITIVITY TO ACTIVATED PROTEIN C

This application is a continuation of application Ser. No. 08/160,877, filed Dec. 3, 1993 now abandoned.

BACKGROUND OF THE INVENTION

The present invention relates to an improved assay for determining the effects of activated protein C ("APC") in test samples to ensure rapid and accurate evaluations. A test sample includes any material that is expected to possess the capability to function with activated protein C. These materials are typically plasma or plasma fractions.

The present assay is based on measuring the conversion of factor X to activated factor X ("factor Xa") by activated factor VIII ("factor VIIIa") present within the test solution. APC inhibits this conversion.

Protein C is a vitamin K-dependent glycoprotein that is synthesized in the liver and circulates in plasma as an inactive zymogen at a concentration of about 4 μg/ml. This protein is converted into an active serine protease (APC) by the thrombin-thrombomodulin complex on the surface of the vessel wall (endothelium). Protein C also may be activated by non-physiologic enzymes, such as the snake-venom factor (Protac C®, Pentapharm, Switzerland)

APC has fibrinolytic properties imparted by its ability to inactivate plasminogen activator inhibitor. APC also has an anticoagulant effect because it can proteolytically degrade factor Va and factor VIIIa. Factor Va is a cofactor for the factor Xa-induced prothrombin activation to thrombin. Factor VIIIa is the cofactor of factor X conversion to factor Xa. As stated above, factor Xa along with factor Va are involved in the conversion of prothrombin to thrombin. Accordingly, the activation of protein C in vivo to form APC constitutes a negative feedback reaction in the generation of thrombin via the degradation of factors Va and VIIIa.

The sensitivity of an individual to the normal activity of activated protein C is defined as "APC sensitivity." APC sensitivities may be evaluated with test samples, such as plasma samples or fractions, obtained from a given individual. Plasma samples or fractions from individuals that are highly sensitive to APC show marked anticoagulation activity when APC is administered. Plasma samples from individuals with decreased APC sensitivity exhibit minimal anticoagulation activity.

A co-factor, protein S, is needed to develop the optimum APC activity. Protein S is a non-enzymatic cofactor for the anticoagulating and pro-fibrinolytic properties of APC. In the plasma, protein S is present in various forms. These forms include a free, active form and an inactive form, which is non-covalently complexed with the C4b-binding protein. In a protein S depleted plasma, APC cannot perform its normal activity. APC will recover its normal activity after addition of protein S.

APC increases the plasma clotting time in a dose-dependent manner. The pathophysiological role of APC is demonstrated in individuals suffering from thrombophilia caused by a congenital protein S or protein C deficiency. Congenital protein S deficiency is autosomal-dominantly inherited, and is characterized by the occurrence of venous and arterial thromboembolisms in early youth. Other adverse effects caused by APC abnormalities include microvascular coagulation, reperfusion injury and septic shock. See Esmon, TCM 2: 214–19 (1992).

A variety of causes may be responsible for decreased APC sensitivity. For example, Dahlbäck et al. have discovered a syndrome characterized by poor anticoagulant response to APC. See Proc. Nat'l Acad. Sci. USA 90: 1004–08 (1993). The blood of patients with this syndrome were found to have normal levels of antithrombin III, protein C, protein S, plasminogen, fibrinogen and other coagulation factors. Dahlbäck et al. postulated that a previously unrecognized cofactor of APC is deficient in the plasma of patients with this syndrome. This syndrome is thought to be inherited. Reliable assays for measuring APC are needed due to the existence of such syndromes.

Tests have been previously developed to assess the blood coagulation disorders of an individual. Methods are described in WO 93/10261. This assay is based on combining an activator of the blood coagulation system with APC and auxiliary agents, such as phospholipids and calcium ions. In this method, the anticoagulant response to human APC is evaluated with factor IXa and factor Xa based coagulation assays. This test is stated to permit detection of disorders not caused by protein S deficiencies of APC resistant factor Va and VIIIa.

The assay of WO 93/10261 involves the entire coagulation cascade, and employs more than one incubation step. This assay requires high concentrations of plasma because it involves the beginning of the coagulation cascade (kallikrein). These concentrations are more than 10% v/v plasma sample, usually as high as 20–35% v/v. The high concentrations of plasma in the reaction mixture permits the factors within the sample to interfere with the assay and thereby decrease its sensitivity and specificity.

Factor VIII activity assays have some applicability in the evaluation of APC sensitivity. One such assay is described in U.S. Ser. No. 07/819,456. The reagent used in this assay contains factor IXaβ, factor X, calcium ions, thrombin, phospholipids and, if desired, factor XIa and factor XIIa. This assay is based on activation of factor X as a function of factor VIII contained in the sample. Factor Xa is then quantitatively determined.

When this assay is used to evaluate proteins that react with factor VIII, such as APC and its cofactor protein S, an excess amount of factor VIII is added to the sample and reacted. The reaction decreases factor VIII activity, and the remaining amount of factor VIII is then determined using a factor VIII chromogenic reagent. In the context of determining APC sensitivity, however, it is desirable to maintain the ratio of substances which influence this activity, such as factor VIII, similar to the levels found in plasma. Additionally, in the context of APC sensitivity this method requires more than one incubation step.

SUMMARY OF THE INVENTION

It is an object of the present invention to provide an improved assay for determining the APC sensitivity of an individual.

It is also an object of the present invention to provide an improved assay for determining APC sensitivity that does not require the addition of factor VIII to a test sample.

It is another object of the present invention to provide an improved assay for determining APC sensitivity that only requires one incubation step.

It is a further object of the present invention to provide an improved assay for determining APC sensitivity that does not involve the entire coagulation cascade.

It is still a further object of the present invention to provide an improved assay for determining APC sensitivity that does not require a determination of all blood coagulation factors present with a test sample.

It is yet a further object of the present invention to provide an improved assay for determining APC sensitivity that requires minimal amounts of test sample to conduct a test.

In achieving these objects, there has been provided, in accordance with one aspect of the present invention, an assay for determining the sensitivity to activated protein C of a test sample, such as a plasma sample or fraction. In accordance with one aspect of the present invention, the assay employs activated factor IX ("factor IXa"), factor X, thrombin, APC, calcium ions and phospholipids. Preferably, the factor IXa is the mature form, known as factor IXaβ. The amount of plasma used according to the present assay need not be above 10% v/v. In a preferred embodiment, the plasma amount used in the assay is less than 2%, and in a more preferred embodiment the plasma amount is 0.8–1.6%.

In accordance with another aspect of the present invention there is provided a method of determining the sensitivity to activated protein C in a test sample, comprising the steps of (a) reacting factor X, activated factor IX, activated protein C and thrombin with the test sample in a test solution containing calcium ions and phospholipids; (b) determining the amount of activated factor X formed in the reaction of step (a); and evaluating the sensitivity of the test sample to activated protein C based on the determination of step (b) as compared to a control. It is preferred that the control involve reacting the test sample with activated factor IX, factor X, thrombin, calcium ions and phospholipids in the absence of activated protein C. The control can also be based on known information, such as a historical control based on established ranges of blood components and activities.

In accordance with still another aspect of the present invention there is provided a test kit for determining the sensitivity of a test sample to activated protein C comprising a first and second reagent component, wherein said first reagent component comprises factor IXa and factor X and said second reagent component comprises activated protein C. Thrombin, calcium ions and phospholipids are present in either said first reagent component or said second reagent component.

In accordance with yet another aspect of the present invention there is provided a test kit for determining the sensitivity of a test sample to activated protein C comprising a first, second and third reagent component, wherein the first reagent component comprises factor IXa, factor X and calcium ions; the second reagent component comprises activated protein C; and the third reagent component comprises phospholipids. Thrombin is also present in the first or third reagent components.

In accordance with still another aspect of the present invention there is provided for determining the sensitivity of a test sample to activated protein C a test reagent comprising factor IXa, factor X, thrombin, activated protein C, phospholipids and calcium ions. Preferably, the test reagent does not contain factor VIII.

DETAILED DESCRIPTION OF PREFERRED EMBODIMENTS

The need has long been recognized for a reliable and accurate assay for determining the APC sensitivity of an individual. Individuals with abnormal APC sensitivity are susceptible to disorders such as thrombosis and thromboembolic diseases. Abnormal APC sensitivity can be caused by protein S deficiency, deficiency or excess of APC inhibitors or cofactors, and APC-resistant factor Va or factor VIIIa. Because abnormal APC sensitivity can be caused by a variety of defects in the blood coagulation cascade, an improved assay should be able to determine APC sensitivity independent of the cause.

The present assay for APC sensitivity is based on the activation of factor X to factor Xa. In the presence of factor IXa and factor VIIIa, factor X is activated to factor Xa. Factor Xa can be detected by using a factor Xa chromogenic substrate. The presence of factor Xa can also be evaluated by the conversion of prothrombin to thrombin or by measuring coagulation time.

The present assay involves adding a test ample, such as plasma sample or fraction, to a solution containing purified factor IXa, factor X, thrombin, APC, calcium ions and phospholipids. Preferably, the mature form of factor IXa, known as factor IXaβ, is used in this assay. Factor IXa, factor X, thrombin, APC, calcium ions and phospholipids can be combined to form a "test reagent," to which the test sample is added to form a "test solution." Factor VIII is not added to the test solution; rather, the factor VIII already present within the test sample is relied upon. Typically, these materials of the test reagent can be prepackaged as two or more "reagent components," and then later combined just prior to adding the test sample. After creation of the test reagent, the evaluation of a test sample can be conducted after a single incubation step.

Because the purified blood factors described above are added to the test solution, the assay can be conducted without relying on the entirety of the coagulation cascade. This permits a simpler and more reliable assay, and permits the use of lower concentrations of test sample. Lowering the amounts of test sample used in the assay minimizes or eliminates the interfering effects exerted by certain blood factors within the sample.

Another advantage of the present assay is that the results are not influenced by anticoagulant therapy with substances, such as coumarine and heparin, which may occur patient's sample undergoing testing. This advantage is important in examining and monitoring patients who are undergoing anticoagulant therapy for thromboembolic disorders. Accurate diagnosis and monitoring of their APC sensitivity status requires that the anticoagulant therapy have no undue effect on the assay results.

The amount of APC to be used in the assay according to the invention should degrade about 50% of the factor VIIIa present in the test sample. A range between 0.05 to 5 U/ml of APC is preferred, the range between 0.2 and 0.4 U/ml being most preferred. The amount of factor VIII present in a test sample can be determined by a variety of means, such as the control of the present assay. The amount of factor VIII in the test sample affects the amount of APC to be used. The amount of factor X used in the assay should be about 0.01 to 10 U/ml.

A tetrapeptide (AcOH-Gly-Pro-Arg-Pro-OH) is often added to the reagent in order to avoid clot formation during the assay. A heparin neutralizing agent, such as polybren, may also be used in the assay.

The present assay does not require the addition of factor VIII. The assay can rely on factor VIII normally present within the test sample as long as the sample contains from 0.3 to 1.5 times the normal amount of factor VIII, which can be determined via the control of the present assay or by other means. The factor VIII present within the test sample is activated by the thrombin added in the assay. Additionally, the test sample or test solution should contain at least 50% of the normal level of protein S, which can be determined via functional assays. Protein S can be added to the test solution in situations where a protein S deficiency in known or suspected, yet an evaluation of other blood factors is desired.

In a preferred embodiment, the assay comprises reacting the test sample with factor X, factor IXa (factor IXaβ), thrombin, calcium ions, and phospholipids in the presence of APC and the absence of APC (control). A test vial containing test sample reacted with factor X, factor IXa (factor IXaβ), thrombin, calcium ions, phospholipids and APC would be evaluated for factor Xa. These results would be compared to the results from a control vial containing test sample reacted with factor IXa (factor IXaβ), factor X, thrombin, calcium ions, phospholipids without the addition of APC. A ratio based on the amount of factor Xa formed in the control divided by the amount factor Xa formed in the test is indicative of the APC sensitivity of the test sample.

Regardless of the cause of abnormal APC sensitivity, the present assay can be used for evaluating the APC effect. For example, the present assay can detect decreased APC sensitivity even where APC resistant factor VIIIa is present. In such a case, the factor VIIIa cannot be degraded by APC, yet the factor VIIIa can still perform its normal functions of converting factor X to factor Xa. This assay is also suitable for detecting abnormalities with regard to the natural inhibitors of APC.

Use of the present assay can be facilitated by prepackaged test kits and reagent components. The factors and other materials are preferably stored with a degree of separation. For example, multi-component test kits for the assay have been developed to assure ease of use and maximum shelf-life.

These test kits preferably comprise two or three reagent components. Three reagent component test kits are preferred because such kits allow for readily available controls because APC is stored separately. Examples of formulations for test kits are set forth below.

The present assay is amenable to practice with a test kit including a first reagent component A and a second reagent component B for producing the reagent according to the invention. The reagent component A contains factors IXa and X and calcium ions and the reagent component B contains thrombin, phospholipids and APC.

A test kit comprising a reagent component C and reagent component D for producing the reagent according to the invention can also be used. Reagent component C contains factors IXa and X, calcium ions and thrombin, and reagent component D contains phospholipids and APC.

The present assay is also amenable to three-component test kits. Three-component test kits having APC as an individual component are preferred because it allows the kit to be readily adapted for evaluating a test sample and a control sample. Because APC would be in its own vial, a control can be undertaken simply by substituting the APC (reagent component) with an equal volume of buffer.

One three component kit comprises a first reagent component E, a second reagent component F and a third reagent component G for producing the reagent according to the invention. Reagent component E contains factors IXa and X and calcium ions. Reagent component F contains thrombin and phospholipids. Reagent component G contains APC.

In the most preferred three component kit, phospholipids are also separated from all other materials. This separation further improves the stability of the reagent components. The preferred three-component kit comprises a first reagent component H, a second reagent component I and a third reagent component J for producing the reagent according to the invention. Reagent component H contains factors IXa and X, calcium ions and thrombin. Reagent component I contains phospholipids. Reagent component J contains APC.

It is preferred to use factor IXaβ in the reagent because it ensures a stable reagent. Factor IXaβ may be obtained from human plasma by standard techniques using Celite® (John-Manville Corp.) The presence of additional coagulation factors XIa and XIIa may also be useful for maintaining the factor IXa activity.

A reagent according to the invention preferably contains factor IXa β in a range of 0.05 and 5 U/ml, factor X in a range of 0.01 and 10 U/ml, thrombin at a concentration ranging between 0.01 and 2.0 U/ml, phospholipids in a range of 0.01 to 100 nmol/ml, calcium ions in a range of 1 to 50 μmol/ml and APC in a range of 0.05–5 U/ml.

It is preferred to use human blood coagulation factors, thrombin and activated protein C. It is further preferred that these components have been subjected to infectious agent inactivation procedures.

The following example contains results from an APC sensitivity determination in various test samples.

EXAMPLE 1

APC Sensitivity Assay With A Three Component Test Kit

The following test kit was employed:
100 μl reagent component H: factor IXaβ, factor X, calcium ions, thrombin and albumin
100 μl reagent component I: Phospholipids and albumin
50 μl reagent component J: Activated protein C (APC) at 2U/ml.

The constituent materials of each reagent component can be prepared in accordance with U.S. Ser. Nos. 07/819,456 and 07/905,541. Other methods of preparing these constituent materials are well known. Commercial sources also exist for obtaining these constituent materials. For example, Components H and I are commercially available under the name IMMUNOCHROM® FVIII:C, IMMUNO AG.

The reagent components are mixed with 50 μl of a plasma sample (1:20 diluted) and incubated for 5 minutes at 37° C. The generated factor Xa is then determined using 200 μl of a diluted chromogenic substrate solution (4 mmol/l $CH_3OCO$-D-CHA-GLy-ARG-pNA-AcOH according to the instructions of IMMUNOCHROM® F VIII: C, IMMUNO AG). This solution also contains α-NAPAP to inhibit thrombin and EDTA to stop further activation of factor X. After 5 minutes incubation, the reaction was stopped with 100 μl of acetic acid (50% in water v/v) for an endpoint method evaluation. The light absorbance was measured at 405 nm to indicate the amount of factor Xa generated during the test. In the control experiment, the plasma sample is incubated with reagent components H and I and 50 μl buffer only. The control lacks added APC. The ratio between the absorbance of the two assay mixtures (without and with APC) is calculated.

EXAMPLE 2

Testing Samples

The following test samples were tested with the three-component test kit of Example I:

(1) Citrated normal plasma-C-npl (sample number: 18)
  Lyophilized Reference Plasma 100% .(IMMUNO AG, Vienna)
  Frozen Normal Control Plasma (George King, US)
  Frozen plasma samples of healthy volunteers (40 –120% of normal factor VIII level)

(2) Heparinized normal plasma—H-npl
Heparin Control Plasma (IMMUNO AG, Vienna)
(3) APC resistant plasma with normal proteins S content:
Control plasma level 2 (Copl2) from the "COATEST APC resistance kit" (Chromogenix, Sweden)
(4) Patient plasma (P), these patients were thrombophilic, but have normal protein C and protein S levels.

| RESULTS | |
|---|---|
| Sample | Ratio (Mean ± SD) |
| C-npl | 1.85 ± 0.09 |
| H-npl | 1.8 |
| Cop12 | 1.49 ± 0.04* |
| P | 1.51 ± 0.04* |

\* — repeated experiments on the same plasma sample

Based on the above experiments, the ratio range for plasma having normal APC sensitivity is 1.65–2.05 (mean ± SD) Values beneath this range are indicative of decreased APC sensitivity. Values above this range are indicative of enhanced APC sensitivity.

It is to be understood that the description and examples provided herein, while indicating preferred embodiments of the present invention, are given by way of illustration and do not limit the present invention. Various changes and modifications may be undertaken without departing from the scope and spirit of the invention.

What is claimed is:

1. A method of determining the sensitivity of a test sample from a human subject to activated protein C, comprising the steps of:
   (a) reacting factor X, activated factor IX, activated protein C and thrombin with said test sample in a test solution containing calcium ions and phospholipids, wherein the amount of endogenous factor VIII in said test sample is at least about 0.3 times the normal amount of factor VIII in plasma;
   (b) determining the amount of activated factor X formed in the reaction of step (a) by measuring the activity of factor Xa using a spectrophotometric substrate specific for said factor Xa; and,
   (c) evaluating the sensitivity of the test sample to activated protein C based on the determination of step (b) as compared to a control,
   wherein said method requires a section of the entire blood coagulation cascade of reactions.

2. A method according to claim 1, wherein said control comprises a control solution made by reacting said test sample with factor X, activated factor IX and thrombin in the presence of calcium ions and phospholipids without the addition of activated protein C, and determining the amount of activated factor X formed thereby.

3. A method according to claim 1, wherein said factor IXa is factor IXaβ.

4. A method according to claim 1, wherein said determining step is performed by adding a chromogenic substrate.

5. A method according to claim 1, wherein the concentration of factor X is 0.01–10 U/ml and the concentration of activated protein C is 0.05–5 U/ml.

6. A method according to claim 5, wherein the concentration of factor IXa is 0.05–5 U/ml and the concentration of thrombin is 0.01–2.0 U/ml.

7. A method according to claim 6, wherein the concentration of phospholipids is 0.01–100 nmol/ml and the concentration of calcium ions is 1–50 μmol/ml.

8. A method according to claim 1, wherein said test sample is less than 10% v/v of said test solution.

9. A method according to claim 8, wherein said test sample is less than 2% v/v of said test solution.

10. A method according to claim 9, wherein said test sample is 0.8–1.6% v/v of said test solution.

11. A test kit for determining the sensitivity of a test sample to activated protein C according to the method of claim 1 comprising a first and second reagent, wherein said first reagent comprises a mixture of factor IXa and factor X and said second reagent comprises activated protein C.

12. A test kit according to claim 11, wherein said first reagent further comprises calcium ions, and said second reagent further comprises thrombin and phospholipids.

13. A test kit according to claim 11, wherein said first reagent further comprises calcium ions and thrombin, and said second reagent further comprises phospholipids.

14. A test kit for determining the sensitivity of a test sample to activated protein C according to the method of claim 1 comprising a first, second and third reagent, wherein said first reagent comprises factor IXa, factor X and calcium ions;

said second reagent comprises activated protein C; and said third reagent comprises phospholipids.

15. A test kit according to claim 14, wherein said first reagent further comprises thrombin.

16. A test kit according to claim 14, wherein said third reagent further comprises thrombin.

17. A test kit for determining the sensitivity of a test sample to activated protein C according to the method of claim 1 comprising a mixture of factor IXa, factor X, thrombin, activated protein C, phospholipids and calcium ions.

18. A test kit according to claim 17, wherein the concentration of factor IXa is 0.05–5 U/ml, the concentration of factor X is 0.01–10 U/ml, the concentration of thrombin is 0.01–2.0 U/ml, the concentration of activated protein C is 0.05–5 U/ml, the concentration of phospholipids is 0.01–100 nmol/ml, and the concentration of calcium ions is 1–50 μmol/ml.

* * * * *